United States Patent [19]

Horwath et al.

[11] Patent Number: 4,467,033
[45] Date of Patent: Aug. 21, 1984

[54] PROCESS FOR OXIDIZING L-SORBITOL TO L-FRUCTOSE

[75] Inventors: Robert O. Horwath, Westport; William J. Colonna, Wilton, both of Conn.

[73] Assignee: Nabisco Brands, Inc., Parsippany, N.J.

[21] Appl. No.: 393,847

[22] Filed: Jun. 30, 1982

[51] Int. Cl.$^3$ ............... C12P 19/02; C12N 15/00; C12N 9/04
[52] U.S. Cl. .................... 435/105; 435/172.1; 435/190
[58] Field of Search ............... 435/105, 190, 172

[56] References Cited

U.S. PATENT DOCUMENTS 3,813,318  5/1974  Armbruster et al. ........... 435/233 X
4,355,103 10/1982  Boguslawski et al. ......... 435/234 X

OTHER PUBLICATIONS

Shaw, Biochemical Journal, vol. 64, pp. 394–405, (1956).
Wang et al., Fermentation and Enzyme Technology, 1979, pp. 47–49.

Primary Examiner—Lionel M. Shapiro
Attorney, Agent, or Firm—Richard Kornutik

[57] ABSTRACT

Process for preparing L-fructose from L-sorbitol by contacting L-sorbitol with D-iditol dehydrogenase produced by a mutant microorganism of the genus Pseudomonas cultivated in the absence of an inducing polyol.

4 Claims, No Drawings

PROCESS FOR OXIDIZING L-SORBITOL TO L-FRUCTOSE

BACKGROUND OF THE INVENTION

This invention relates to a process for preparing L-fructose alone or in admixture with polyols, such as L-mannitol and L-sorbitol.

L-sugars are useful as sweetening agents because, as disclosed in U.S. Pat. No. 4,262,032, they are sweet like the D-sugars, but unlike D-sugars, L-sugars are either not metabolized by the body or are metabolized to a lesser extent than the D-sugars. These features make L-sugars desirable as sweeteners for individuals wishing to reduce caloric-intake or for individuals unable to metabolize common sugar sweetening agents without detrimental effects, e.g., diabetics. Another advantage associated with L-sugars is the absence of an objectionable aftertaste commonly experienced with artificial sweeteners such as saccharin and the cyclamates. However, as desirable as the L-sugars are in the foregoing respects, their relative scarcity in nature, particularly L-glucose and L-fructose, the laevo counterparts of the two monosaccharide sweeteners most commonly used today, has prevented their widespread use in foods and beverages or even their being considered for use in such products.

D. Shaw, "Polyol Dehydrogenases", *Biochem. J.*, 64 (1956), pp. 394–405, the contents of which are incorporated by reference herein, describes the oxidation of D-gulitol, a polyol identical to L-glucitol and L-sorbitol, by employing D-iditol dehydrogenase isolated from a species of Pseudomonas cultivated in a nutrient medium containing dulcitol which is required to induce the microorganism to produce the enzyme. The need for dulcitol, which must be extracted from certain plants or obtained by hydrogenation of lactose, imposes a considerable limitation on the practical usefulness of the Shaw process.

SUMMARY OF THE INVENTION

In accordance with the present invention, L-sorbitol is oxidized to L-fructose by employing D-iditol dehydrogenase isolated from or present in a mutant strain of microorganism which is capable of producing D-iditol dehydrogenase in the absence of an inducer, and is selected from the genus Pseudomonas.

The foregoing mutant strain of microorganism is obtained by exposing a culture of a selected microorganism to chemical or physical mutagens such as ethyl methane-sulfonate, nitrosoguanidine or 8-azaguanine, or by irradiation with ultraviolet light, gamma-rays or x-rays. An example of obtaining a mutant strain of a microorganism capable of producing xylose isomerase without an inducer by ultra-violet irradiation is found in U.S. Pat. No. 3,813,318 to Armbruster, et al., the contents of which are incorporated by reference herein. Methods generally known in the art are used to determine which individual colonies from the resulting culture are capable of producing D-iditol dehydrogenase in the absence of an inducer. The mutant microorganisms which have the desired characteristic are isolated by conventional microbiological techniques.

DESCRIPTION OF THE PREFERRED EMBODIMENTS

The starting L-polyol for the process herein, L-sorbitol, is not a naturally occurring substance, but can be obtained by hydrogenation of L-glucose. Since L-glucose is relatively scarce in nature, it is preferred in the present invention to obtain L-glucose by the chemical treatment of L-arabinose, a naturally occurring sugar which is available in significant quantities from sugar beet pulp by the method described in *Chemical Abstracts:* 142135v, Vol. 75, 1971 (Czech. Pat. No. 137,537), the contents of which are incorporated by reference herein. According to this method, dry sugar beet pulp is treated with sulfuric acid to obtain an extract solution which is subsequently fermented, evaporated and filtered. L-arabinose is thereafter crystallized from the resulting filtrate.

L-glucose can be obtained from L-arabinose by the method of Sowden and Fischer, *J.A.C.S.*, Vol. 69 (1947), pp. 1963–1965, the contents of which are incorporated by reference herein. In accordance with this method, L-arabinose is condensed with nitromethane in the presence of sodium methoxide to provide sodium salts of the nitroalcohols. The sodium salts are readily converted to the corresponding sugars by means of the Nef reaction. The Sowden-Fischer conversion of L-arabinose to L-glucose is represented by the following equations:

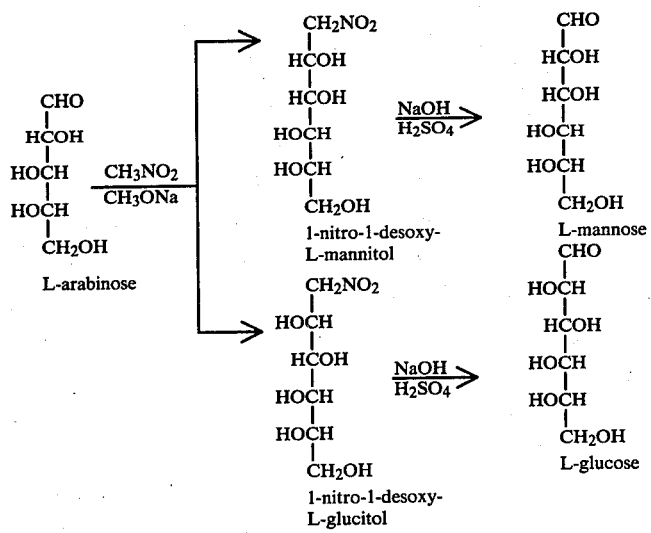

In addition to the Sowden-Fischer method, L-glucose can also be made by the Kiliani-Fischer synthesis which is described in, amongst other, *Organic Chemistry* by Morrison and Boyd (2d ed. 1966), pp. 990–911, the contents of which are incorporated by reference herein. According to the Kiliani-Fischer method, L-arabinose is converted into two glyconic acids of the next higher carbon number by condensation with hydrocyanic acid and hydrolysis of the resulting cyanohydrins. The glyconic acids are then reduced to the corresponding aldoses. The Kiliani-Fischer synthesis of L-glucose from L-arabinose is illustrated by the following equations:

hydrogenating the L-sugars to L-sorbitol and L-mannitol.

L-sorbitol can be obtained from L-glucose by hydrogenation methods known in the art, for example, as described in U.S. Pat. No. 4,173,514 to Kruse, the contents of which are incorporated by reference herein. In accordance with the method described in U.S. Pat. No. 4,173,514, L-glucose and L-mannose are catalytically hydrogenated to L-sorbitol and L-mannitol using catalysts and reaction conditions known in the art. The hydrogenation is ordinarily carried out at super-atmospheric pressure at a temperature within the range of about 100° C., to about 160° C., and at a mildly acidic to

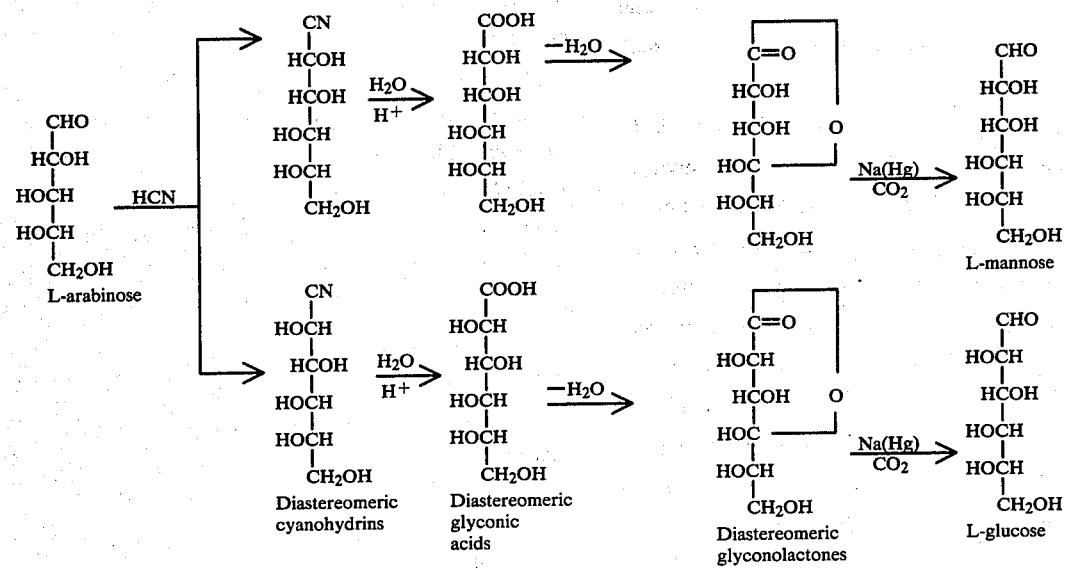

Both synthetic procedures provide L-glucose in admixture with L-mannose. The L-glucose can be separated from the L-mannose, e.g., by differential crystallization in either a free or derivatized state, or by separation using ion-exchange techniques. However, for reasons of economy, it is preferred to employ the mixture of the two sugars in the present invention without attempting to isolate or concentrate the L-glucose before neutral pH. Examples of preferred catalysts are supported nickel catalysts and supported ruthenium catalysts.

The polyol dehydrogenase utilized in the present invention can be obtained from a microorganism of the genus Pseudomonas which produces D-iditol dehydrogenase. A fluorescent species of Pseudomonas is known to be a good source of the D-iditol dehydrogenase.

The selected microorganism is mutagenized by exposure to chemical or physical mutagens such as ethyl methane-sulfonate, nitrosoguanidine, or 8-azaguanine, or by irradiation with ultraviolet light, gamma-rays or x-rays.

The treated cells are then propagated by generally known methods until the cell number has increased at least about 25 fold. The treated cells are plated out, and each colony is tested by art-recognized procedures for D-iditol dehydrogenase activity, e.g., the mutagenized colonies can be individually cultivated in test tubes, and, subsequently, by known methods cells from each colony are harvested, lysed and tested for the presence of L-fructose. Since the medium on which the colonies are grown does not contain dulcitol or any other polyol to induce the production of D-iditol dehydrogenase enzyme, only those colonies having the desired characteristics will show a positive enzyme reaction.

A very preferred method of testing for D-iditol dehydrogenase activity is to press a circular disc of filter paper moistened with 25 mM phosphate buffer (pH 8) containing a permeabilizing agent such as disodiumethylenediaminetetraacetic acid and lysozyme mixture, Triton X-100, Tween 80, cetyltrimethylammonium bromide, deoxycholic acid, and the like onto the plates of treated cells to pick up the microbial colonies by adsorption. Since D-iditol dehydrogenase is intracellular, a permeabilizing agent is required so that L-mannose will freely penetrate into the cells to react with the enzyme, and so that L-fructose formed therefrom can freely diffuse out of the cells where it can be detected. A "sandwich" of the microbes is formed by placing the first disc of filter paper colony-side down onto a second disc of filter paper moistened with the above solution plus 10% L-sorbitol.

The paper sandwich is pressed between two clean glass plates and incubated at 30° C. for a period of time necessary for oxidation of L-sorbitol to L-fructose to occur. The paper sandwich is disassembled and air-dried. The papers are then sprayed with acidic naphthoresorcinol for ketose detection. The development of pink spots is a positive test for keto-sugar, i.e., L-fructose and, therefore, D-iditol dehydrogenase. Colonies corresponding to these positive zones on the filter paper are then located by reference to the original master plates and isolated by conventional microbiological techniques.

The cells having the desired characteristics are cultivated from about 12 to about 72 hours under aerobic conditions at about 25° to 35° C. at a pH between 6 and 8 in an aqueous nutrient medium containing potassium phosphate, trace metals, Difco yeast extract and agar, with shaking.

Once the cells have multiplied a desired number of times, they are harvested by methods known in the art, e.g., washing with a NaCl solution to remove the agar, centrifuging, rewashing with the NaCl solution and suspending the cells in known solutions, such as a potassium phosphate buffer solution.

The sorbitol oxidation is carried out by utilizing art recognized procedures to immobilize the cells containing D-iditol dehydrogenase or to rupture the cells, for example, through contact with a lysing agent, such as toluene, or through ultra-sonic treatment. If the cells are ruptured to release the intracellular L-sugar isomerase, a cell-free extract containing the enzyme is obtained by known methods and the extracellular enzyme can be immobilized in accordance with known and conventional procedures. For example, the enzyme can be immobilized on various particulate silica material including glass or ceramic-based materials, natural or synthetic polymers such as cellulose, e.g. diethylaminoethyl cellulose, and various known organic polymer supports known in the art.

The oxidation of L-sorbitol to L-fructose is effected in a buffered enzyme solution, e.g., phosphate buffer (pH 8.0) or glycine buffer (pH 10.0), at about 25° C. for a length of time which can be readily determined experimentally. If a cell-free extract of the enzyme is employed, a hydrogen acceptor, e.g., nicotinamide adenine dinucleotide (NAD), in the presence of an accessory hydrogen carrier, e.g., methylene blue, is added to the enzyme solution. If whole cells of the mutated microorganism are utilized, a hydrogen acceptor is not required, but the presence of an accessory hydrogen carrier, e.g., methylene blue is preferable. The reaction temperature selection will be predicated on the thermal stability of the enzyme system employed, the more thermally stable systems permitting higher reaction temperatures. Of course, the reaction time will, in part, be determined by the reaction temperature. As would be expected, the higher the temperature, the shorter the reaction time period for the desired degree of reaction. In enzymatic reactions of the present type, equilibrium will be reached in reasonable time periods, usually ranging from as little as 30 minutes up to several hours, and even longer. As is recognized in this art, the progress of the reaction can be followed by removal of aliquots from the reaction mixture and analyzing for product and/or starting substrate, thus, permitting optimization of reaction parameters for the specific enzyme system employed. The enzyme system may vary depending on the microorganism from which the enzyme is obtained, and the method of isolation and purification, if employed.

Once equilibrium is established, the isomerization reaction is essentially completed and the enzyme is removed from the reaction mixture solution by art recognized procedures, e.g., by denaturing the enzyme and removing the denatured protein by centrifugation, or separation of immobilized enzyme by physical means, e.g., filtration.

In an embodiment of the present invention, L-sorbitol in admixture with L-mannitol is oxidized to L-fructose by D-iditol dehydrogenase. Subsequently, L-mannitol and unreacted L-sorbitol are separated from L-fructose using various techniques familiar to those skilled in the art. For example, a strong-base anion exchanger converted to the borate form and washed with dilute borate solution may be employed to separate negatively charged borate complexes resulting from borate reacting with the polyols and saccharide. The use of borate solutions at a high pH, i.e., between 8 and 9, as eluting agents are ordinarily favored since borate as the replacing ion shifts the equilibrium of the borate ion - sugar or polyol reaction towards the complex form of the sugar or polyol, and the high pH minimizes the total amount of borate required for the separation. By experimental methods, one can determine the conditions under which L-fructose is selectively eluted from the ion-exchange columns, and collect the fraction containing L-fructose. L-fructose is ultimately recovered from the borate-sugar complex in accordance with the method described in U.S. Pat. No. 3,689,362 or other art-recognized techniques. According to the method described in U.S. Pat. No. 3,689,362, a solution of the borate-sugar complex is either treated with a cation exchange resin, or with a mineral acid so as to bring the pH of the solution to below 3. Since the borate-sugar complex is unstable under acidic conditions, particularly when the solution temperature is reduced to below about 10° C., the borate compound decomposes into boric acid and the corresponding inorganic salt, and the boric acid precipitates from the solution. Any residual boric acid and the dissolved inorganic salt can be separated from the L-fructose solution by methods known in the art, e.g., ion-exchange techniques, electrodialysis, and the like. L-fructose can also be recovered from the borate-sugar complex by passing the cooled effluent through a cation exchange column in the acid form to remove any cations, evaporating the purified solution at reduced pressure, chilling the concentrate to about 0° C. so that most of the boric acid precipitates out and can be removed from the solution by filtration, and finally passing the concentrate through an anion exchange resin in the base form to remove any residual acid.

Another possible method of separating L-fructose from the L-polyols is to add phenylhydrazine to the mixture solution, thereby forming L-fructose phenylhydrazone which precipitates out of the solution leaving behind L-mannitol and L-sorbitol. L-fructose is then regenerated from the precipitate by known techniques.

In another embodiment of this invention, L-sorbitol is separated from L-mannitol prior to the enzymatic oxidation process by the crystallization of L-mannitol from an aqueous polyol solution as described in U.S. Pat. No. 3,632,656 to Unver, the contents of which are incorporated by reference herein. This method includes seeding a hot, aqueous, concentrated solution of L-sorbitol and L-mannitol with L-mannitol crystals in plate form. As the temperature of the solution is cooled from above the saturation temperature for mannitol to below said saturation temperature, mannitol crystallizes and is filtered out of the aqueous solution.

Once L-mannitol is removed from the reaction system, L-sorbitol is oxidized to L-fructose. Unreacted L-sorbitol is separated from the L-fructose by known techniques, e.g., the ion-exchange treatment or phenylhydrazine treatment as described above. However, the separation step is unnecessary if the oxidation reaction is essentially driven to completion by adding to the reaction mixture a borate compound which selectively complexes with L-fructose. U.S. Pat. No. 3,689,362 to Takasaki, the contents of which are incorporated by reference herein, shows a procedure for increasing the D-fructose yield in the enzymatic isomerization of D-glucose by employing glucose isomerase in the presence of a borate compound. Suitable borate compounds are water-soluble borates, such as sodium or potassium borate, and water-insoluble or slightly soluble borates, such as magnesium and barium borate. Anion-exchange resins in the borate form can also be used in the present invention. To obtain the maximum oxidation ratio, an optimum concentration of borate to be added can be determined experimentally. Factors to be taken into consideration include the L-sorbitol concentration and the type of borate selected. Since the borate compound forms a borate-sugar complex with L-fructose, L-fructose is removed from the reaction system, and the oxidation equilibrium shifts driving the oxidation reaction essentially to completion.

EXAMPLE

A. Preparation and selection of mutant strains

A 25-ml culture of *P. fluorescens* in a mineral medium containing 0.25% $KH_2PO_4$, 0.01% $MgSO_4$ $7H_2O$, 0.1% $(NH_4)_2SO_4$, 0.01% Difco yeast extract, 2% agar, and 0.5% glucose is harvested and washed by centrifugation, then resuspended in 5 ml of mineral medium without glucose.

The cells are irradiated with an ultraviolet light source at a distance of about four inches for about eight minutes. The treated cells are recovered and washed, then resuspended with 5 ml of mineral medium without glucose. A 0.5 ml aliquot of the suspension is inoculated into 100 ml of mineral medium with 0.5% glucose and incubated overnight at 30° C. with shaking to allow a 25-50 fold increase in cell number.

Small aliquots (0.1-0.2 ml) of the resulting culture are inoculated into agar plates containing the mineral medium with 0.5% glucose, then incubated for 18-24 hrs. at 30° C. Colonies which appear on these master plates are replica-plated onto fresh agar plates containing the same medium and incubated at 30° C. for 18-24 hrs. A circular disc of filter paper moistened with 25 mM phosphate buffer (pH 8) is pressed down onto the replica plates to pick up the microbial colonies by adsorption. The paper is removed and placed colony-side down onto a second filter paper disc moistened with the above solution plus 10% L-sorbitol, forming a "sandwich" with the microbes between the papers.

The paper sandwich is pressed between two clean glass plates and incubated at 30° C. for a period of time necessary for oxidation of L-sorbitol to L-fructose to occur. The paper sandwich is disassembled and air-dried. The papers are then sprayed with acidic naphthoresorcinol for ketose detection. The development of pink spots is a positive test for keto-sugar, i.e., L-fructose and, therefore, D-iditol dehydrogenase. Colonies corresponding to these positive zones on the filter paper are then located by reference to the original master plates and isolated by conventional microbiological techniques.

B. Oxidizing L-sorbitol to L-fructose

Cells of the mutant strain of *P. fluorescens* having the desired trait are harvested by centrifugation after growing .02M potassium phosphate buffer (pH 7.4). They are disrupted in a sonic oscillator equipped with an ice-water cooling jacket and the cellular debris is removed by centrifugation. The remaining supernatant solution is the cell-free extract containing D-iditol dehydrogenase.

The reaction mixture containing 1 mmole of L-sorbitol, 50 ml of 25 mM phosphate buffer (pH 8), 3 mmoles of NAD, methylene blue and cell-free extract (20-50 mg of protein) is incubated for 2-3 hours at 30° C., or until equilibrium is established. The reaction mixture is then heated in a boiling water bath, and the denatured protein removed by centrifugation.

While the present invention has been described in connection with specific embodiments thereof, it is understood that it is capable of further modifications and adaptations as will be readily understood by those skilled in the art.

We claim:

1. A process for oxidizing L-sorbitol to L-fructose which comprises contacting L-sorbitol with D-iditol dehydrogenase produced by a mutant microorganism of the genus Pseudomonas cultivated in the absence of an inducing polyol.

2. A process according to claim 1, wherein the microorganism is *Pseudomonas fluorescens*.

3. A process according to claim 1, wherein the L-sorbitol is in the form of an admixture with L-mannitol obtained by catalytically hydrogenating L-glucose in admixture with L-mannose under effective reactive conditions.

4. A process for oxidizing L-sorbitol to L-fructose which comprises:
 (a) subjecting a microorganism of the genus Pseudomonas to a mutagenizing agent;
 (b) isolating a mutant strain of the microorganism having the ability to produce D-iditol dehydrogenase in the absence of an inducing polyol; and
 (c) oxidizing L-sorbitol to L-fructose by employing D-iditol dehydrogenase produced from said mutant strain under L-sorbitol oxidizing conditions.

* * * * *